(12) United States Patent
Secco et al.

(10) Patent No.: US 12,127,849 B2
(45) Date of Patent: Oct. 29, 2024

(54) DEVICE AND METHOD FOR DETECTING AND MONITORING CUTANEOUS DISEASES

(71) Applicant: Politecnico Di Torino, Turin (IT)

(72) Inventors: Jacopo Secco, Turin (IT); Marco Farina, Turin (IT)

(73) Assignee: Politecnico Di Torino, Turin (IT)

( * ) Notice: Subject to any disclaimer, the term of this patent is extended or adjusted under 35 U.S.C. 154(b) by 710 days.

(21) Appl. No.: 17/296,103

(22) PCT Filed: Nov. 13, 2019

(86) PCT No.: PCT/IB2019/059735
§ 371 (c)(1),
(2) Date: May 21, 2021

(87) PCT Pub. No.: WO2020/104896
PCT Pub. Date: May 28, 2020

(65) Prior Publication Data
US 2022/0008002 A1   Jan. 13, 2022

(30) Foreign Application Priority Data

Nov. 23, 2018   (IT) ........................ 102018000010536

(51) Int. Cl.
*A61B 5/00* (2006.01)
*A61B 5/01* (2006.01)
*A61B 5/389* (2021.01)

(52) U.S. Cl.
CPC ............ *A61B 5/445* (2013.01); *A61B 5/0077* (2013.01); *A61B 5/01* (2013.01); *A61B 5/389* (2021.01);
(Continued)

(58) Field of Classification Search
CPC ......... A61B 5/445; A61B 5/0077; A61B 5/01; A61B 5/389; A61B 5/443; A61B 5/6844;
(Continued)

(56) References Cited

U.S. PATENT DOCUMENTS

| 2003/0167008 A1* | 9/2003 | Rogers ................... A61B 5/445 600/474 |
| 2017/0173262 A1 | 6/2017 | Veltz |

FOREIGN PATENT DOCUMENTS

| WO | 2014/172671 A1 | 10/2014 |
| WO | 2015/059636 A1 | 4/2015 |
| WO | WO-2018204249 A1 * | 11/2018 ............... A61B 5/01 |

OTHER PUBLICATIONS

Dawid Polap et al., *An Intelligent system for Monitoring Skin Disease*, Sensors, 2018, vol. 18, pp. 1-20.
(Continued)

*Primary Examiner* — Gary Jackson
*Assistant Examiner* — Sebastian X Lukjan
(74) *Attorney, Agent, or Firm* — Workman Nydegger

(57) ABSTRACT

A device and a method are provided for detecting and monitoring cutaneous diseases, wherein the device includes an image acquisition component adapted to acquire medical images of at least one portion of skin affected by a cutaneous disease, sensors adapted to detect physical conditions of the portion of skin and/or environmental conditions around the portion of skin, and to generate pathology data representing the physical conditions and/or the environmental conditions, memory for storing data in digital form, and a processor configured for a) reading the pathology data detected by the sensors and the medical images acquired by the image acquisition component, and b) storing the pathology data and the medical images into the memory.

15 Claims, 5 Drawing Sheets

(52) U.S. Cl.
CPC ............ *A61B 5/443* (2013.01); *A61B 5/6844* (2013.01); *A61B 5/7264* (2013.01); *A61B 2560/0242* (2013.01); *A61B 2562/0271* (2013.01); *A61B 2562/029* (2013.01)

(58) Field of Classification Search
CPC .......... A61B 5/7264; A61B 2560/0242; A61B 2562/0271; A61B 2562/029; Y02A 90/10; G16H 30/40; G16H 50/20
See application file for complete search history.

(56) References Cited

OTHER PUBLICATIONS

International Search Report and Written Opinion dated Mar. 5, 2020, issued in PCT Application No. PCT/IB2019/059735, Nov. 13, 2019.
Communication Pursuant to Article 94(3) EPC dated Jun. 5, 2024, issued in EP Application No. 19801984.6.

* cited by examiner

DEVICE AND METHOD FOR DETECTING AND MONITORING CUTANEOUS DISEASES

BACKGROUND OF THE INVENTION

1. The Field of the Invention

The present invention relates to a device and a method for detecting cutaneous diseases, e.g., an ulcer, an erythema or the like; in particular, the present invention makes it possible to detect the cutaneous disease and to evaluate the status thereof, e.g., the degree of inflammation and/or the degree of bacterial or viral infection.

2. The Relevant Technology

As is known, the skin is the first barrier that is used by the human body in order to protect itself from the outside environment.

Those people who are compelled to spend much time in the same position (e.g., physically disabled or elderly persons with deambulation problems, who are often confined to bed or need to use a wheelchair) or in remote areas of the planet (e.g., soldiers, people living in tribes, volunteers working for humanitarian organizations, or the like) are often affected by cutaneous diseases (e.g., decubitus ulcers, erythemas caused by allergies or mycoses, wounds caused by insect stings or animal bites, etc.), which may be due to reduced skin elasticity (e.g., because of excessive stasis or malnutrition) or to living in an environment that inevitably involves contact with animals, fungal spores or plants which, when touched, produce a skin reaction that may degenerate into a cutaneous disease requiring appropriate medical-dermatological treatments.

Access to such treatments is however difficult for these people; in fact, without a careful diagnosis by a dermatologist, there is a risk that a skin treatment will not solve the problem, but will simply attenuate the effects thereof (as is the case, for example, when a simple cortisone-based cream is used in order to reduce the effects of an acute urticaria caused by an allergic reaction, without however knowing the allergen) or that damages will be caused to the patient's skin (e.g., when a cortisone-based cream is used in order to treat a mycosis).

It is therefore clear that, without a high-quality diagnosis made by a dermatology specialist, these people are bound to suffer from chronic skin diseases; such problems may degenerate into very serious pathologies, e.g., formation of deep ulcers that may require the amputation of a limb to save the patient's life.

SUMMARY OF THE INVENTION

The present invention intends to solve these and other problems by providing a device for detecting cutaneous diseases.

Furthermore, the present invention intends to solve these and other problems by also providing a method for detecting cutaneous diseases.

The basic idea of the invention is to acquire, through image acquisition means, medical images (i.e., images acquired by using a specific procedure) of at least one portion of skin affected by a cutaneous disease, and to detect, through sensor means, physical conditions (e.g., the temperature of the skin, or the like) of said portion of skin and/or environmental conditions (e.g., the temperature and/or humidity of the environmental air) around said portion of skin, so as to generate pathology data representing said physical conditions and/or said environmental conditions.

Medical images and pathology data are thus made available to the dermatologist, who will be able to make a more accurate diagnosis than would be possible by only examining the medical images, i.e., the specialist will also be able to estimate the status of the cutaneous disease. In fact, knowing the physical conditions of the portion of skin and/or the environmental conditions around it, it will be possible for the dermatologist to identify the disease(s) with better precision and to evaluate the status of said disease more accurately without having to actually visit the patient.

It must be pointed out that a cutaneous disease that causes a skin erythema may reveal itself differently depending on the temperature and/or humidity of the environment around the patient or the patient's complexion type, etc. Therefore, the use of additional pathology data along with the medical image will allow the dermatologist to better comprehend the clinical context the patient is in and to identify the most appropriate therapy. For example, in a tropical climate preference will be given to therapies using creams containing antibiotic substances in order to reduce bacterial proliferation, which is promoted by high temperature and humidity values.

Further advantageous features of the present invention are set out in the appended claims.

BRIEF DESCRIPTION OF THE DRAWINGS

These features and further advantages of the present invention will become more apparent in the light of the following description of an embodiment thereof depicted in the annexed drawings, which are provided merely by way of non-limiting example, wherein.

DETAILED DESCRIPTION OF THE PREFERRED EMBODIMENTS

In this description, any reference to "an embodiment" will indicate that a particular configuration, structure or feature is comprised in at least one embodiment of the invention. Therefore, the phrase "in an embodiment" and the like, which may be present in different parts of this description, will not necessarily be all related to the same embodiment. Furthermore, any particular configuration, structure or feature may be combined in one or more embodiments in any way deemed appropriate. The references below are therefore used only for simplicity's sake, and do not limit the protection scope or extension of the various embodiments.

Figure 1:
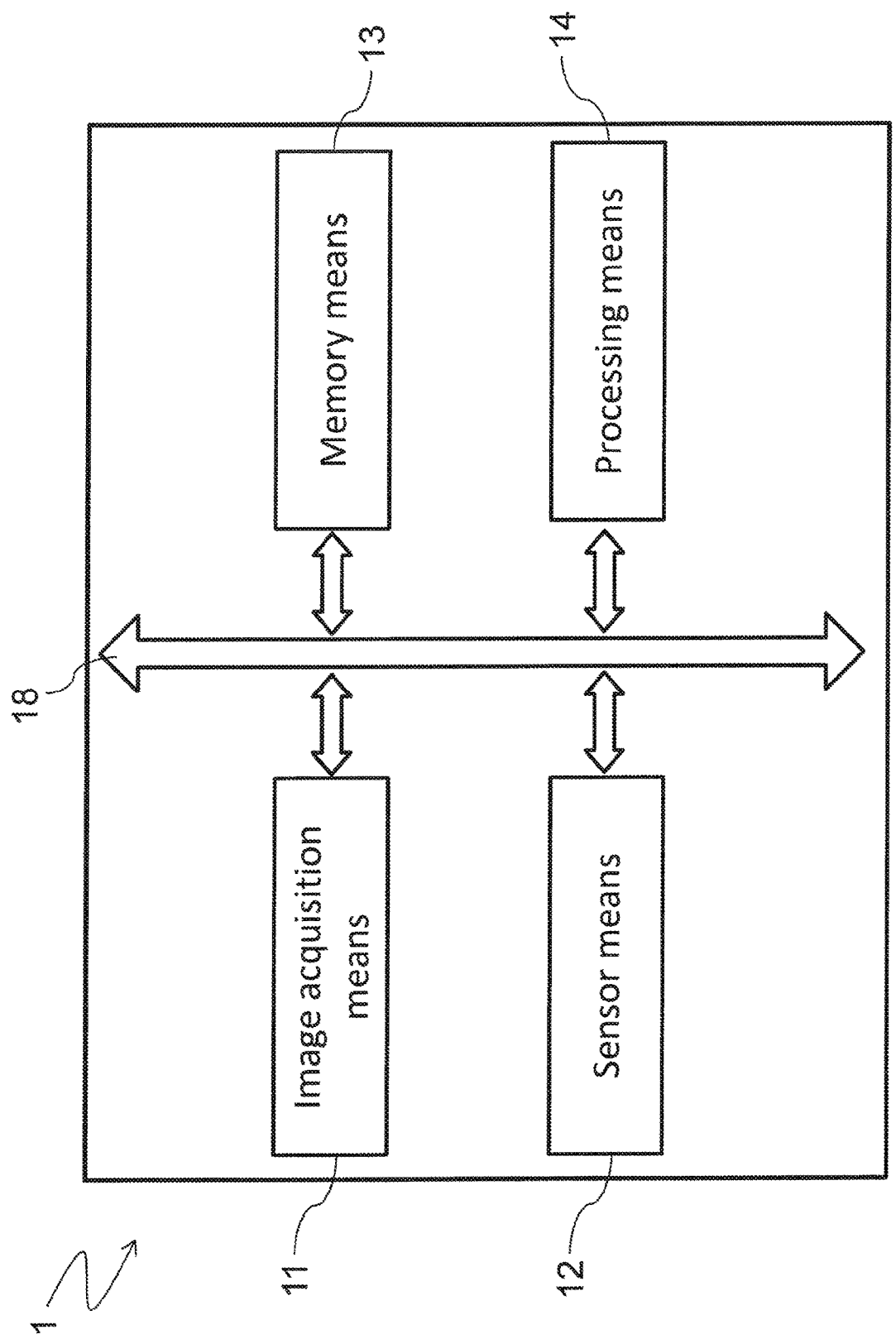
FIG. 1 shows a block diagram of an apparatus for detecting cutaneous diseases according to the invention.

With reference to FIG. 1, the following will describe an embodiment of a device 1 for monitoring cutaneous diseases according to the invention; said device comprises the following parts:

image acquisition means 11 (e.g., a CMOS image acquisition sensor preferably having a known focal curve and/or an autofocus function and/or an automatic aperture adjustment function and/or an automatic exposure adjustment function) adapted to acquire medical images of at least one portion of skin affected by a cutaneous disease. Such acquisition means are preferably equipped with optical lenses that permit taking macro images and/or selectively filtering the wavelengths as will be further described below. Such lenses may be either fixedly or movably coupled to the optics and the sensors of the acquisition means 11;

sensor means 12 adapted to detect physical conditions of the portion of skin (e.g., a thermal camera, an electronic nose, a humidity sensor, or the like) and/or environmental conditions around said portion of skin (e.g., a thermometer and/or a hygrometer for measuring the air temperature and/or humidity), and to generate pathology data representing said physical conditions and/or said environmental conditions;

memory means 13 (e.g., a RAM, SSD, HDD memory or the like) for storing data in digital form, e.g., the pathology data and/or a set of instructions implementing a method for monitoring cutaneous diseases according to the invention;

processing means 14 (e.g., a CPU, a GPU, a microcontroller, an FPGA or the like) in communication with the image acquisition means 11, the sensor means 12 and the memory means 13;

a communication bus 18, which allows the exchange of data in wired mode (e.g., via USB) and/or in wireless mode (e.g., via Wi-Fi or Bluetooth) among the processing means 14, the memory means 13, the sensor means 12 and the image acquisition means 11.

As an alternative to the communication bus 18, the processing means 14, the memory means 13, the sensor means 12 and the image acquisition means 11 may be connected by means of a star architecture.

In the most general embodiment, the processing means 14 (and hence also the entire device 1) are configured for executing the following steps:

reading the pathology data detected by the sensor means 12 and the medical images acquired by the image acquisition means 11;

storing said pathology data and said medical images into said memory means 13.

In this way, the dermatologist or general practitioner can use medical images as well as pathology data to produce a diagnosis that is more accurate than would be possible by only examining the medical images.

More in detail, the device 1 is preferably implemented in two distinct preferred embodiments for collecting the pathology data required by the dermatologist in order to make a diagnosis.

Both embodiments of the device 1 execute the method for detecting cutaneous pathologies according to the invention.

Figure 2:
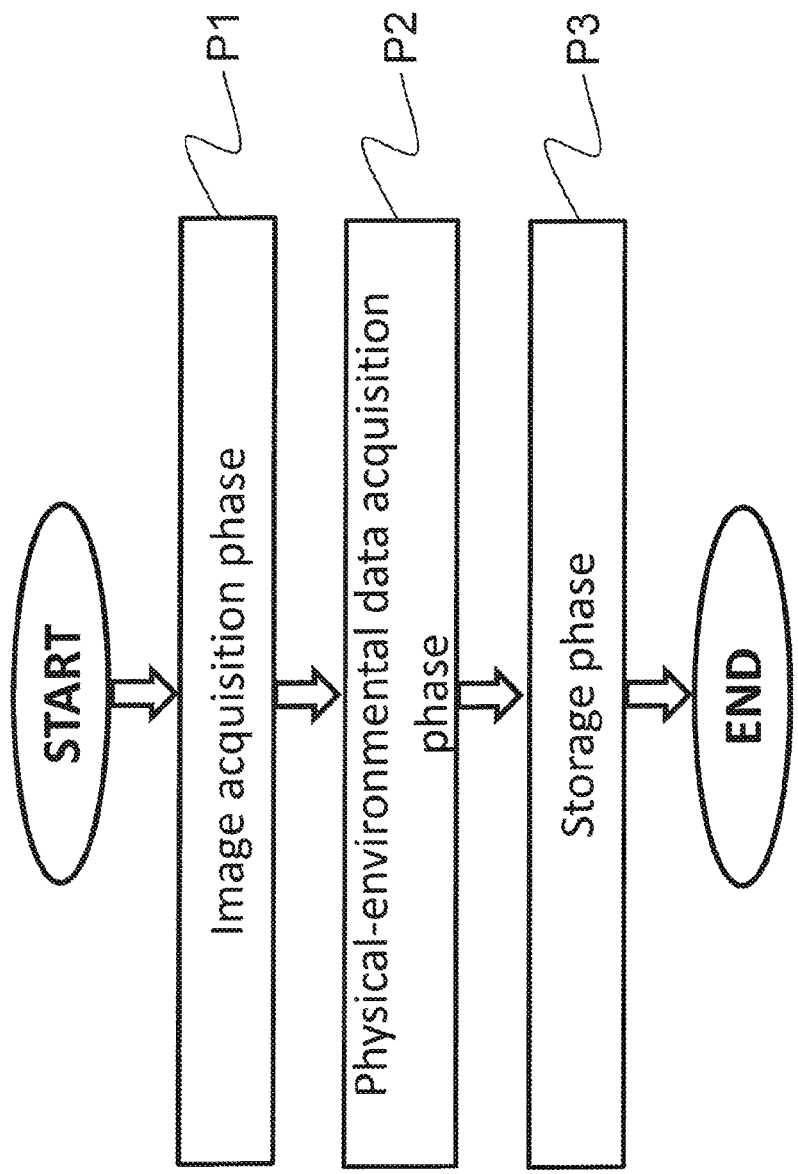
FIG. 2 shows a flow chart of a method for detecting cutaneous diseases according to the invention.

Also with reference to FIG. 2, the method according to the invention comprises the following phases:

an image acquisition phase P1, wherein medical images of at least one portion of skin affected by a cutaneous disease are acquired by the image acquisition means 11;

a physical-environmental data acquisition phase P2, wherein physical conditions (e.g., physiological data) of said portion of skin and/or environmental conditions around said portion of skin are detected by the sensor means 12, and pathology data are generated which represent said physical conditions and/or said environmental conditions;

a storage phase P3, wherein the pathology data detected by the sensor means 12 and the medical images acquired by the image acquisition means 11 are read by the processing means, and said pathology data and said medical images are stored into memory means 13.

In this way, the doctor can use medical images along with pathology data, so as to be able to produce a more accurate diagnosis than would be possible by only examining the medical images.

The first configuration of the device 12, also referred to as stand-alone configuration, preferably comprises a printed circuit board comprising a crown, preferably having a radius in the range of 2 to 5 cm, including at least three white LED lights preferably arranged equidistant along the perimeter of the crown, wherein said image acquisition means 11 are positioned at the centre of said crown. In this embodiment, the sensor means preferably comprise at least one of the following configurations of elements for measuring the distance and the three-dimensional profile of the lesion, positioned according to criteria that will be described below, and anyway such that and in such a number that they can detect the distance of the device from the wound and from the periphery (i.e., the skin area around the wound):

a) one or more optical (e.g., infrared or laser-light sensors) and/or acoustic (e.g., ultrasonic, also known as PING ultrasonic sensors) distance sensors, which can be positioned according to a regular and symmetric geometry with respect to the image acquisition means 11; such sensors should be positioned preferably within or anyway not farther than 5 cm from said image acquisition means 11;

b) at least one DLP micromirror sensor placed in proximity to the image acquisition means 11. This sensor makes it possible to detect the difference in pixel brightness through the fading effect and, based on such difference, processing means can compute the distance between the image acquisition means 11 and the portion of skin affected by the disease;

c) at least one structured light emitter with the associated sensor, arranged in proximity to the image acquisition means 11, so that the processing means can estimate the depth of a skin lesion on the basis of an image (acquired by the image acquisition means 11) of a portion of skin illuminated by said structured light;

d) second image acquisition means (e.g., a CMOS sensor comprising variable optics) with an automatic focus (autofocus) function, wherein said second image acquisition means are positioned in proximity to the first ones 11, so that the processing means can be configured for estimating the distance on the basis of the focal distance of the second image acquisition means, without changing the focal distance of the image acquisition means 11.

In other words, the sensor means 12 comprise one or more distance sensors capable of measuring a distance between said portion of skin and said device. This allows the dermatologist to better evaluate the dimensions of the dermatological pathology illustrated in the medical images, so that he/she will be able to make a diagnosis of higher quality than would be possible by only evaluating the medical images.

The device 1 preferably comprises also an internal or removable battery capable of supplying power to the above-described components; in addition, said device 1 may also be powered by an external power source via a cable and/or a coil capable of generating sufficient current to power the device 1 when a sufficiently high variable magnetic field is flowing through it (electromagnetic induction power supply method).

In addition to the above, the device 1 may comprise interfacing means (e.g., a USB, Bluetooth, IEEE 1394 interface, or the like) in communication with the memory means 13. This allows an external computer (e.g., a Personal Computer used by a dermatologist for reporting purposes) to gain access to the images and pathology data, so that the dermatologist can view the images appropriately (preferably on a reporting monitor capable of adequately reproducing colours for medical use) and analyze the pathology data by using suitable software application packages.

In particular, the interfacing means may comprise a video interface (e.g., VGA, DVI, HDMI or the like) to be connected to a screen (preferably an active matrix display) that may be either comprised in the device 1 or external to said device 1, so as to allow the dermatologist to view the medical images and pathology data also in the absence of a dedicated reporting workstation.

As an alternative to or in combination with the above, the device 1 may comprise communication means, e.g., an IEEE 802.11 (WiFi), IEEE 802.16 (WiMAX), IEEE 802.15 (Bluetooth) interface, or the like. Moreover, the processing means 14 may be configured for transmitting, via said communication means, the acquired medical images and pathology data. In this way, it will not be necessary to send the device 1 or the memory means 13 of said device 1 to the dermatologist, and the dermatologist will be able to make a diagnosis regardless of his/her own position. For example, the dermatologist may be thousands of kilometres away from the location where a qualified operator (e.g., a nurse or a general practitioner) or the patient him/herself is using the device 1 to acquire the images and the pathology data. Thus, the dermatologist may even make a diagnosis in an interactive manner (e.g., in video conference), suggesting to the qualified operator or the patient how the device 1 should be used.

In addition to the above, the processing means 14 of the device 1 may also be configured for acquiring the images and/or the pathology data, via said image acquisition means 11 and/or said sensor means 12, on the basis of acquisition data stored in the memory means 13, which specify how the images and/or the pathology data must be acquired by the device 1. For example, the acquisition data may specify the exposure time and/or the aperture to be used by the image acquisition means 11, or whether or not an autofocus function and/or an exposure adaptation function, which automatically adjusts the exposure time, should be used, or the light wavelength to be used in order to illuminate the cutaneous lesion through the sensor means 12, or the like.

In other words, the memory means 13 may contain at least acquisition data specifying how (during the image acquisition phase P1 and/or the physical-environmental data acquisition phase P2) the images must be acquired by said image acquisition means 11 and/or the physical and/or environmental conditions that must be detected by said sensor means 12, the image acquisition means 11 being configured, preferably via the processing means 14, for acquiring the medical images on the basis of said acquisition data and/or the sensor means 12 being configured, preferably via the processing means 14, for detecting the physical conditions of said portion of skin and/or the environmental conditions around said portion of skin on the basis of said acquisition data.

Furthermore, the acquisition data may preferably be generated remotely by the dermatologist by means of a suitable application and received by the device 1 via the communication means.

This reduces the risk of errors by the dermatologist caused by improper use of the device 1, thus allowing the dermatologist to make a more accurate diagnosis because the risk of errors caused by incorrect acquisition of the images is reduced; in fact, if the dermatologist cannot be understood by the patient or operator because of language problems (e.g., because the user of the device 1 does not speak the same language as the dermatologist) and/or cultural differences (e.g., because the user of the device 1 cannot comprehend what the dermatologist is saying and/or is not able to configure the device 1), the transmission of appropriate acquisition data will make it possible to configure the device 1 in such a way as to ensure that it will operate correctly.

As an alternative to or in combination with the above, the sensor means may comprise at least one sensor capable of detecting physiological parameters of the patient; such sensors may be either connected to the board (and hence also to the processing means 14) by means of suitable connectors or directly integrated into the printed circuit (e.g., by soldering). These sensors include the following types:

an ultraviolet image sensor capable of detecting light having a wavelength in the range of 200 to 450 nanometres and one or more sources of ultraviolet light (e.g., a Wood's lamp, also known as UV lamp), so as to enable the detection of the fluorescence of some bacterial or viral species; said sensor may also be implemented by applying a polarized optical filter (with a fixed or removable frame) to the image acquisition means 11, so as to filter the light in such a way as to only allow light having a wavelength below 480 nm to pass, thus eliminating any signal crosstalk phenomena. This will allow the dermatologist to produce a diagnosis of higher quality;

an infrared image sensor, e.g., an NIR CMOS camera capable of detecting light having a wavelength in the range of 650 to 1,200 nanometres and one or more infrared light sources, preferably of the "near" infrared type (NIRS), capable of emitting a beam having a wavelength in the range of 650 to 1,200 nm; said infrared image sensor can preferably work at a sampling frequency of at least 100 Hz and preferably comprises a polarized optical filter (with a fixed or removable frame) calibrated to the same wavelengths (650-1,200 nanometres), so as to eliminate any signal crosstalk phenomena and allow the dermatologist to produce a diagnosis of higher quality;

at least one electronic nose adapted to recognize volatile compounds emitted by said portion of skin affected by a cutaneous disease (e.g., the presence of ammonia, typically indicating the presence of ulcers, and/or other volatile compounds that are emitted in the presence of specific bacterial species, which will be further described below), so as to allow the dermatologist to produce a diagnosis of higher quality, since said electronic nose allows for (remote) detection of the presence of substances that can hardly be detected by a human nose even during a dermatologic visit, when the dermatologist can inspect the patient's skin in person;

one or more thermal sensing devices (e.g., an infrared thermometer, a thermal camera, or the like), also referred to as thermal sensors, positioned in such a way as to be able to sense the surface temperature of the portion of skin affected by the cutaneous disease;

at least one electronic environmental humidity and temperature sensor and/or skin humidity sensor capable of sensing the humidity of said portion of skin affected by the cutaneous disease, so as to allow the dermatologist to better evaluate the appearance and status of a cutaneous disease, and hence produce a diagnosis of higher quality than would be possible by only evaluating the images.

As an alternative to or in combination with the above, the device 1 comprises a data entry interface (e.g., a keyboard, a touchscreen capable of displaying a keyboard, a microphone, or the like) in communication with the processing means 14, which may be configured for acquiring patient data (e.g., the phototype of the patient's skin, the patient's sex, age, weight, etc.) and storing them into the memory means 13.

This makes it possible for the dermatologist to produce a diagnosis of higher quality, because a greater amount of data is made available to the physician.

As an alternative to or in combination with the above, the sensor means may comprise an electromyographic unit comprising the following elements:

- a pair of cutaneous electrodes for collecting electric surface biosignals, preferably of the dry-disk or silver chloride (AgCl) type and having a surface not smaller than 0.5 mm$^2$;
- a signal generator adapted to generate an alternating current electric signal, preferably with a sinusoidal or square wave, adjustable up to a maximum value of 40 Volt peak-to-peak (Vpp) and having a maximum frequency of 1 Hz, so as to advantageously generate a current having an intensity not exceeding 50 µA, or not exceeding 10 µA if the patient has cardiac catheters or an implanted pacemaker or a cardiac defibrillator (also known as ICD), thus advantageously avoiding any risk of a microshock;
- measuring means, e.g., am ammeter and/or a voltmeter, capable of acquiring an electromyographic signal (e.g., by sensing one or more of its characteristics, such as intensity, voltage, phase, frequency and/or the like) generated by the electric current flowing through the pair of electrodes, and transmitting said electromyographic signal, preferably in digital form, to the processing means 14.

This makes it possible for the dermatologist to produce a diagnosis of higher quality, because an electromyographic signal is made available to him/her which can provide interesting information about the state of the peripheral nervous system, the operation of which can be influenced by the presence of a particular cutaneous disease.

Of course, numerous variants of the example described above are possible.

The following will describe a second embodiment of a device according to the invention; for brevity's sake, the following description will only highlight those parts which differentiate this and the next variants from the above-described main embodiment.

The second embodiment of the device according to the invention is a general purpose device, such as, for example, a mobile terminal (e.g., a smartphone or the like), a tablet, a laptop, a personal computer or the like, to which the above-described image acquisition means and sensor means can be connected via input/output means (e.g., via USB, Bluetooth or the like), and wherein said device is configured for executing a set of instructions implementing the method for monitoring cutaneous diseases according to the invention.

Figure 3:
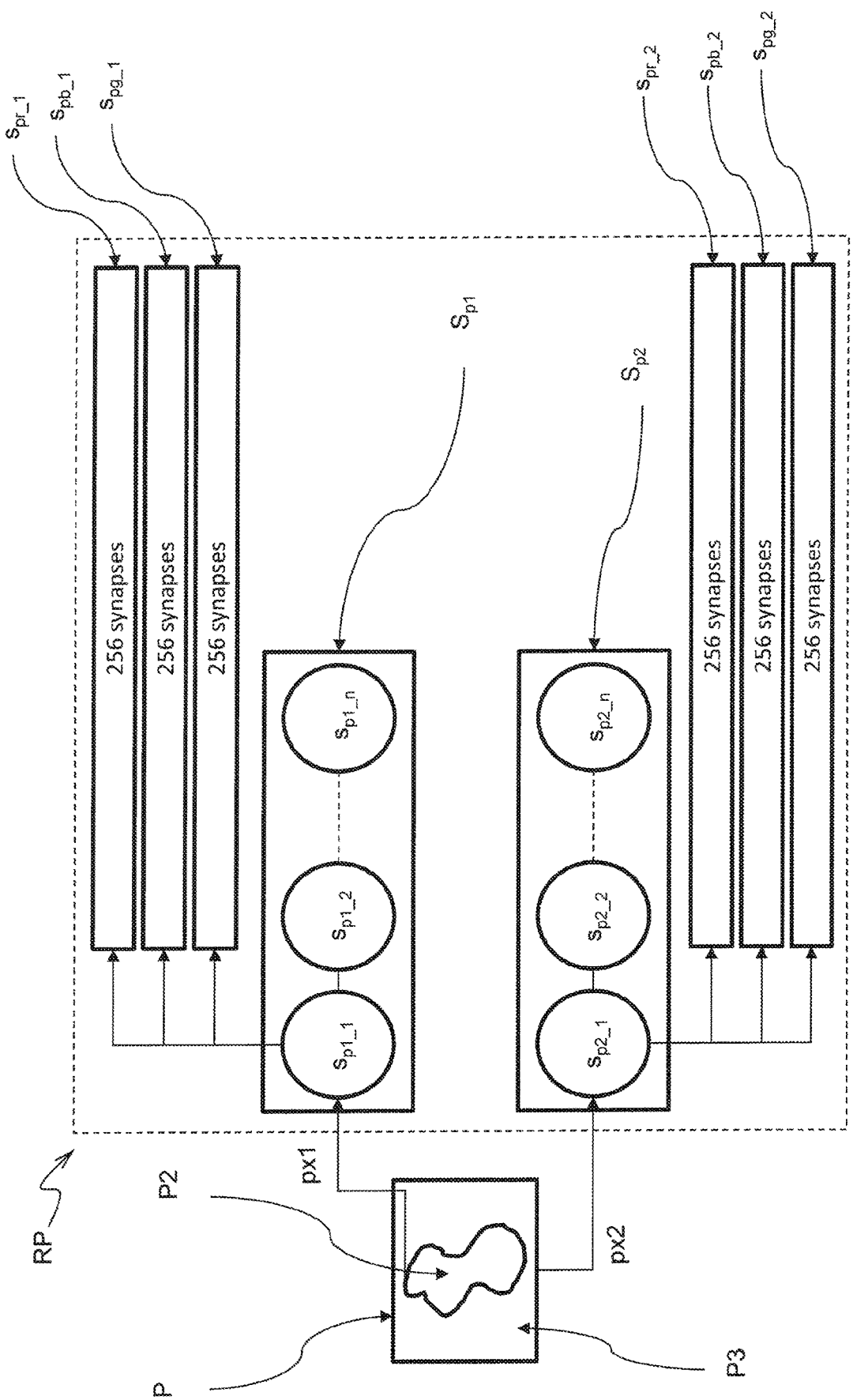
FIGS. 3, 4 and 5 show partial graphic representations of neural networks implemented within at least one embodiment of the invention.

Also with reference to FIG. 3, an image P depicting a first portion of damaged skin P2, preferably affected by a cutaneous disease, and a second portion P3 surrounding the damaged portion P2 (also known as "periphery") can be analyzed by means of a first neural network RP, preferably of the feedforward type, implemented through the processing means 14 or other processing means (e.g., comprised in a server, in the dermatologist's personal computer, or the like), which preferably execute a set of instructions implementing said neural network RP. This neural network RP has been trained for outputting a typology datum, which defines the typology of the cutaneous disease, on the basis of the acquired images (inputted to said network). In this way, the dermatologist can speed up the diagnosis process by using this typology datum, because such datum will allow him/her to narrow the field of investigation in less time, excluding a priori other types of tests to which the patient could be subjected, so as to produce a diagnosis (and the resulting therapy) in less time. This is well suited for the context of use of the device 1 of the invention, because the dermatologist may have to analyze images and pathology data collected by different devices 1 in the field, thus having to produce a plurality of diagnoses in the shortest time possible.

The neural network RP preferably comprises two layers $S_{p1}, S_{p2}$ of computational nodes (which will also be referred to below as "synapses" $S_{p1\_1}, \ldots, S_{p1\_n}$ and $S_{p2\_1}, \ldots, S_{p2\_n}$, the number of which depends on the number of lesion typologies into which the analyzed images are to be discretized. It must be pointed out that the number of synapses $S_{p1\_1}, \ldots, S_{p1\_n}$ and $S_{p2\_1}, \ldots, S_{p2\_n}$ in each one of the layers $S_{p1}$ and $S_{p2}$ must be the same. The synapses of each layer Sp1 and Sp2 are respectively connected to three vectors ($s_{pr\_1}, s_{pg\_1}, s_{pb\_1}$ for the first layer $S_{p1}$ and $s_{pr\_2}, S_{pg\_2}, S_{pb\_2}$ for the second layer $S_{p2}$), each one preferably containing 256 synapses.

It must be highlighted that, if the neural network RP is not present, then the lesion typology must be entered by the user via the interfacing means.

Figure 4:
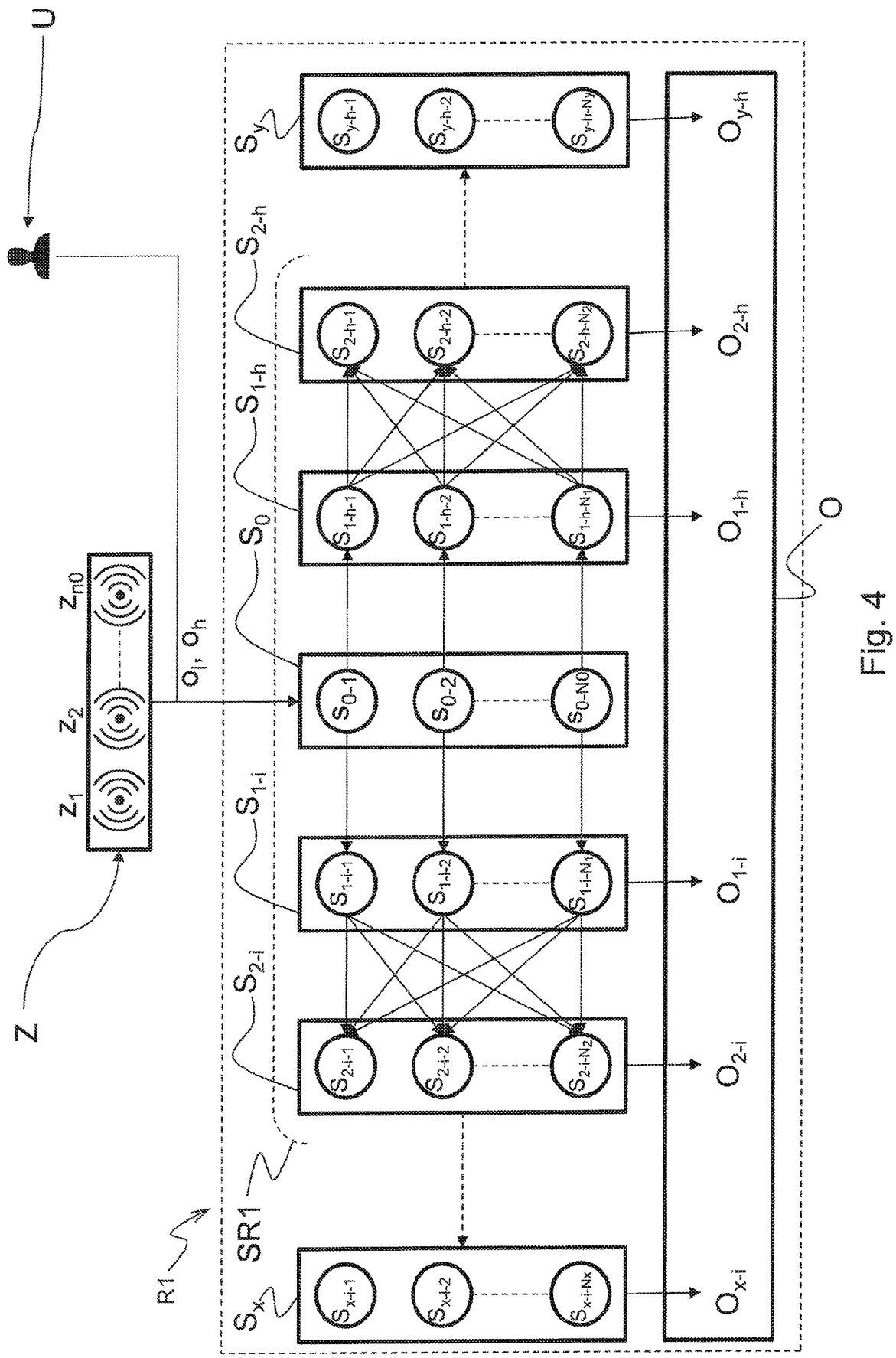
Figure 5:
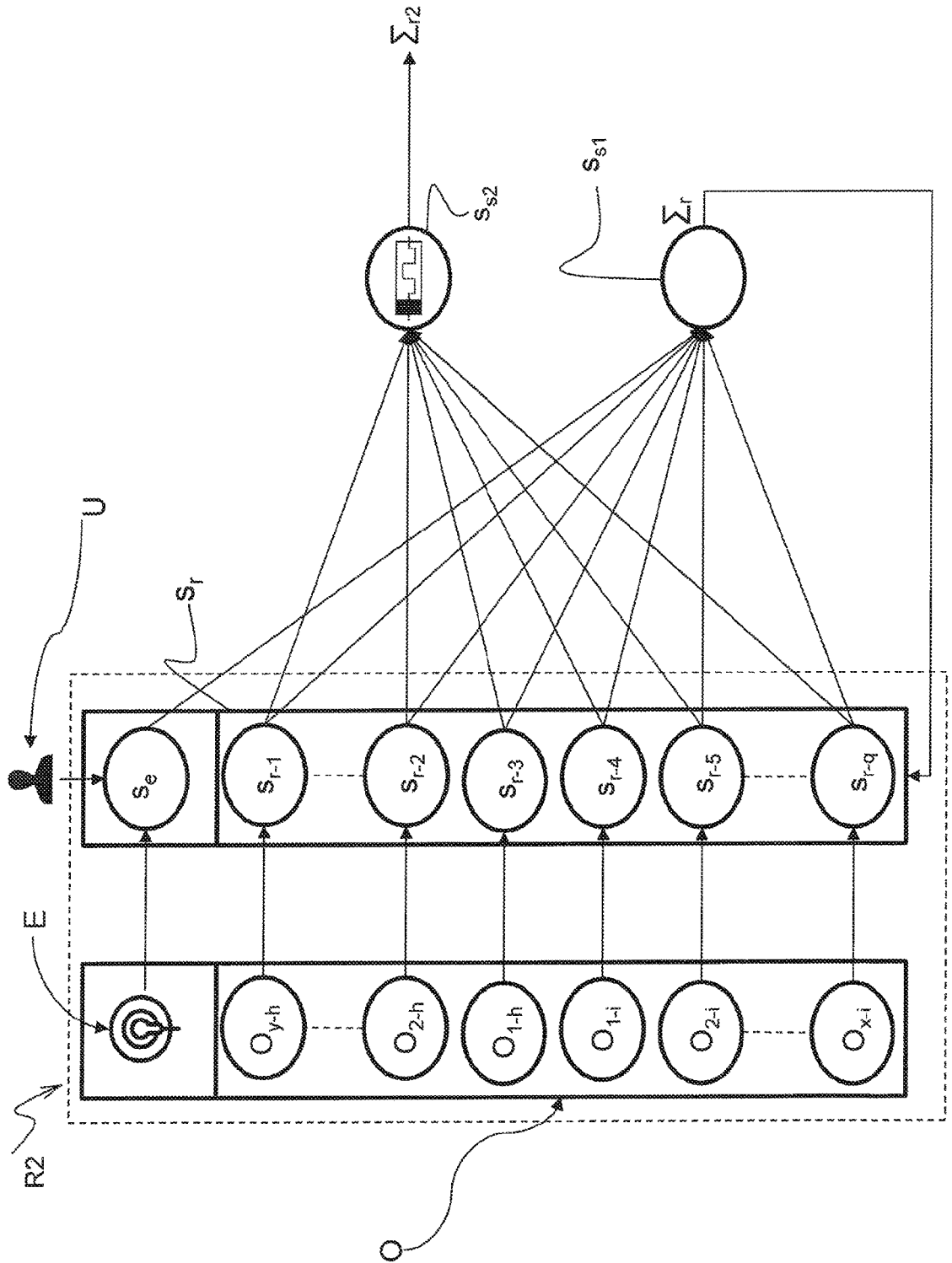

Also with reference to FIGS. 4 and 5, the data detected by the sensor means 12, the use of which will be described later on, may be processed through the use of a second neural network R1 and a third neural network R2, wherein each one of them can be implemented (just like the first neural network RP) through the processing means 14 of the device 1 or through other processing means (e.g., those comprised in a server, in the dermatologist's personal computer, or the like).

The function of the second neural network R1 is to process the data directly collected by the sensor means 12 in order to establish a possible inflamed and/or infected condition of the lesion caused by the disease, while the third neural network R2 is a network designed to process the data generated by R1 in order to calculate the degree of infection and/or inflammation, and may be added to the device or system when one wants to read and interpret the generated data.

The second network R1 is a neural network, preferably of the perceptron type, designed to execute a deep learning operation; said network R1 comprises at least five vectors SR1 comprising computational nodes or synapses. The central vector $S_0$ performs the task of receiving a vector Z of values $z_1, \ldots, z_{n0}$ inputted to the neural network SR1; such values come from the above-mentioned sensor means 12 included in the configuration of the device. The number of synapses of the layer $S_0$ is defined on the basis of the typology of the sensor means 12 included in the device; in particular, the number of synapses may preferably be selected on the basis of the following scheme (adding up the number of synapses associable with each one of the sensor means 12 comprised in the device 1):

- if the sensor means 12 comprise the UV light source, the neural network SR1 may have a number of synapses in the range of one to six;
- if the sensor means 12 comprise the infrared light source, the neural network SR1 may have a number of synapses amounting to at least one;

if the sensor means 12 comprise the electronic nose, the neural network SR1 may have a number of synapses in the range of one to x, where x is the number of volatile compounds that the electronic nose can recognize;

if the sensor means 12 comprise said one or more thermal sensors, the neural network SR1 may have a number of synapses amounting to at least one;

if the sensor means 12 comprise the electronic humidity sensors, the neural network SR1 may have a number of synapses amounting to at least one.

The layer $S_0$ is connected to at least 2 other layers of synapses, referred to as first-line layers, $S_{1-i}$, $S_{1-h}$: the first first-line layer $S_{1-i}$ is preferably dedicated to detecting the infection status, while the second first-line layer $S_{1-h}$ is preferably dedicated to detecting the inflammation status, each one having a number of synapses equaling that of the layer $S_0$. Each one of the layers $S_{1-i}$ and $S_{1-h}$ is in turn connected to at least one further layer $S_{2-i}$ and $S_{2-h}$, also referred to as second-line layer. The number of synapses of the second-line layers $S_{2-i}$, $S_{2-h}$, depends on the number of synapses of the layer $S_0$ and hence on the number of synapses of the first-line layers $S_{1-i}$, $S_{1-h}$. Considering a number of synapses $N_0$ in $S_0$ equal to the number of synapses $N_1$ of each first-line layer, the number of synapses $N_2$ of each second-line layer $S_{2-i}$, $S_{2-h}$ amounts to $N_1(N_1-1)$. The same rule applies to any other layers following the second-line ones. Considering $S_X$ as the line of the layer for which the number of synapses $N_X$ has to be calculated, the following relation will apply:

$$N_X = N_{X-1}(N_{X-1}-1)$$

The connections between the synapses of the layers $S_0$ and $S_1$ are univocal, i.e., each synapse of the layer $S_0$ is connected to only one synapse of the layer S1. The connections between the synapses of the layers S1 and S2 are such that each synapse of the preceding layer has a connection in common with all other computational nodes of its layer in the next layer. As concerns any other layers following the second-line ones, the connections between their synapses and the synapses of the preceding layers must follow the same logic as the preceding layers. Each layer of the network produces an operational output $O_{X-i}, \ldots, O_0, \ldots, O_{y-h}$, thus generating at least five values to be read for verifying the lesion infection status, the lesion inflammation status, or both.

In other words, the processing means 14 or the external processing means may be configured for executing a portion of code implementing the second neural network R1 trained to produce, on the basis of said pathology data, pathology status data defining if said portion of skin affected by said cutaneous disease is infected and/or inflamed. In this way, the dermatologist can produce a diagnosis of higher quality in the same time, because he/she will not have to re-interpret the data coming from the sensor means 12 whenever a diagnosis needs to be made (possibly by also consulting some medical textbooks), but he/she can delegate part of this process to the second neural network, which has preferably been trained under his/her supervision to provide one or more possible answers that will then necessarily have to be interpreted by the dermatologist.

The output values of the second neural network R1 are then read by the third neural network R2, the function of which, as previously described, is to evaluate the degree of the inflamed or infected condition of the lesion under examination. The neural network R2 relates the values provided by the network R1 to either an electromyographic signal E generated by the electromyographic unit or patient data acquired via the data entry interface.

In other words, the processing means 14 may be configured for executing a portion of code implementing the third neural network R2, which is trained to produce, on the basis of the pathology status data (produced by the second neural network R1) and said electromyographic signal E (produced by the electromyographic unit), a pathologic degree datum defining the degree of the infection and/or inflammation of said portion of skin affected by said cutaneous disease.

In this way, the dermatologist will be able to produce a diagnosis of higher quality in the same time, because he/she will not need to re-interpret the data coming from the sensor means 12 whenever a diagnosis needs to be made, but can delegate part of this process to the third neural network, which has preferably been trained under his/her supervision to provide one or more possible answers, which will then necessarily have to be interpreted by the dermatologist.

The third neural network R2 is preferably designed as a single-layer feedforward network $s_r$ formed by at least 5 synapses $S_{r-1}, \ldots, s_{r-q}$ plus an additional synapse $s_e$. Each operational output O of the second neural network R1 is distinctly inputted to one of the synapses $S_{r-1}, \ldots, S_{r-q}$. Therefore, when increasing the number of layers of the neural network R1, it will be necessary to increase the number of synapses $s_{r-1}, \ldots, s_{r-q}$ of the third neural network R2 to the same extent. Each synapse $s_{r-1}, \ldots, s_{r-q}$ is respectively connected to two nodes $S_{S1}, S_{S2}$: the first node $S_{S1}$ is an adder node, to which also the synapse $s_e$ is connected, whereas the second node $S_{S2}$ is a relation node, the operation of which will be described below.

The purpose of the device 1 described herein, in both of its embodiments, is to detect both the typology of the lesion (if the neural network Rp is present) and the possible inflammation and/or infection status of a cutaneous lesion, while optionally also determining the degree thereof. This is done by using the images taken by the image acquisition means 11 and the data acquired by the sensor means 12 and subsequently processed by the networks R1 and, optionally, R2. Each one of them must initially be subjected to a training phase using the same data generated by the image acquisition means 11 and/or by the sensor means 12, depending on the network involved. This phase calibrates the values associated with the synapses of all the layers that make up the neural networks RP, R1 and R2. When the training phase is over, the networks can enter the operating phase, in which the networks can autonomously process the data collected by the image acquisition means 11 and by the sensor means 12. In this phase, the values associated with the synapses are not changed. More than one training phase may be carried out, e.g., whenever synapses are added to the network layers or whenever a layer is added to the network R1. A new training phase may also be started when it is believed that the networks have not yet reached an appropriate level of processing sensitivity or sensibility. It must be reminded that, if the network RP is not present in the system, the operator will have to enter the typology of the lesion under examination via the data entry interface of the device.

When the device 1 is in an operating condition, said device is pointed towards the lesion, parallel to the plane of the body region involved, preferably through the use of the image acquisition means, which may help the operator frame the cutaneous lesion correctly; after this, at least one photograph of the lesion and of a surrounding skin portion, to be used as a reference, is taken by the image acquisition means 11, preferably by exploiting the light produced by at least one of the crown LEDs. As the picture is taken, the acquired images have to be collected and stored into the memory means 13 of the device 1. Through the sensor means 12, whether simultaneously or after taking the photograph, also the physiological data of the lesion are collected. For such data to be read by the network R1, they must preferably be digitalized. Each one of said physiological data will be considered as an input z to the network R1. Each input is associated with one node of the layer $S_0$ that receives it.

The following will accurately describe some examples of utilization of the physiological data collected by each typology of sensor means 12, as previously described, as well as the associated methods for acquiring said physiological data.

When the sensor means 12 comprise the ultraviolet image sensor and said one or more ultraviolet light sources, it is possible to acquire an image (preferably by using the optical filter) that will allow detecting the presence and quantity of some bacterial or viral species. The following is an incomplete list of cutaneous diseases producing skin lesions that reflect ultraviolet light, thereby producing light of a particular colour:

Tinea capitis (mycotic infection) emits blue/green light;
Tinea versicolor (mycotic infection) emits yellow/green/orange light;
erythrasma (bacterial infection) emits red light;
vitiligo (cellular death) emits white light;
Porphyria cutanea tarda (pathology of genetic origin or caused by particular environmental conditions) emits red/pink light;
Pseudomonas infezione (bacterial infection) emits green light;
acne (bacterial infection) emits orange/red light;
Corynebacterium minutissimum (bacterial infection) emits red light.

The image taken is preferably coded by using an RGB code and analyzed pixel by pixel, considering the portion of the image that comprises the lesion and a small skin region adjacent thereto (periphery). The detection of each colour (six in total: yellow, green, blue, red, orange, pink) is associated with a specific input vector Z, so that, as previously described, the synapses associated with the UV light source may be 6 at most, depending on the number of colours that the system has been designed to detect and compute. For each value, the proportion between the pixels of the image having that specific colour and the total pixels of the image portion under examination is computed. If this ratio exceeds a threshold (which is preferably adjustable and has a minimum limit of, preferably, 0.5%), then the z associated with that colour will be 1, otherwise it will be 0.

When the sensor means 12 comprise the infrared image sensor and said one or more infrared or "near" infrared (NIRS) light sources, it is possible to detect the quantity of oxygenated hemoglobin in relation to deoxygenated hemoglobin. This value indicates a physiological activation of the body region that comprises the lesion, thus indicating a possible inflammation condition thereof. Irradiation of the IR or NIR diodes can be activated starting from a minimum distance of 1 cm. By irradiating the area of the lesion and the periphery with IR or NIR light within a wavelength range of 760 nm (value of maximum absorption of light by deoxygenated hemoglobin) to 900 nm (value of maximum absorption of light by oxygenated hemoglobin) and by detecting the output signal by means of the NIR CMOS camera, it is possible to count the number of points representing the skin portions that absorb a 760 nm wavelength and those that absorb a 900 nm wavelength, so that one can know the respective quantities of both in the area of interest. It must be pointed out that the absorption (A) of IR or NIR light is calculated for each wavelength according to the Lambert-Beer law as follows:

$$A = \log(I_{inc}/I_{ril})$$

where $I_{inc}$=incident light, $I_{ril}$=detected light.

The input given to the competent synapse of the layer $S_0$ will be 1 if $(A_{900\,nm} - A_{760\,nm})/A_{760\,nm}$ is greater than or equal to a given adjustable threshold with a lower limit preferably set to 0.1%.

When the sensor means 12 comprise said at least one electronic nose, the device 1 can detect the presence of one or more volatile compounds, such as the following:
a. Ammonium;
b. Isoprene;
c. Acetic acid;
d. Ethanol;
e. Dimethyl disulphide;
f. Hydrogen sulphate (sulphuric acid);
g. Acetone;
h. Acetaldehyde;
i. Methyl thiocyanate;
j. Hydrogen cyanide;
k. Formaldehyde;
l. Butanol.

These volatile compounds come from various viral species that may be found in the area of a cutaneous lesion. Such species include, among others, Escherichia coli, Pseudomonas and Staphylococcus. The bacterial and viral flora that can be found by detecting volatile compounds is extremely large, and it has been demonstrated that the same is true for the range of volatile compounds generated thereby and detectable through an electronic nose. The electronic nose(s) included in the present system must be configured to detect the presence of at least one of the volatile compounds that can be scientifically associated with bacterial or viral elements. The presence of each one of the volatile compounds is associated with an input z, which is read by the specific synapse of the layer $S_0$ of the second neural network R1. For each one of the compounds for which the electronic nose(s) has (have) been configured, an adjustable threshold value is set. If the detection of that specific compounds exceeds said threshold, then the respective resulting z will have the value of 1, otherwise it will be 0.

When the sensor means 12 comprise said one or more thermal sensing devices, it is possible to detect the temperature in the area of the lesion and in the neighbouring regions. A temperature in the area of the lesion higher than that in the peripheral regions suggests the presence of an inflammatory condition. Considering $T_F$ as the average temperature of the damaged area, and $T_P$ as the average temperature in the area around the wound, if the ratio $(T_F - T_P)/T_P$ exceeds an adjustable threshold with a minimum limit preferably set to 0.1%, then the input z associated with the specific synapse of the layer $S_0$ of the second neural network R1 associated with the thermal sensing device will preferably have a value of 1, otherwise it will have a value of 0.

When the sensor means 12 comprise the electronic humidity sensor capable of sensing the presence and quantity of exudate in the area of the lesion, it is possible to detect if the value returned by the humidity sensor exceeds an adjustable threshold (with a minimum limit greater than 0) and then send to the specific synapse of the layer $S_0$ of the second neural network R1, preferably, the value 1 as input Z in the event that the humidity value exceeds said threshold, or the value 0 otherwise.

As aforesaid, the number of inputs Z sent to the network R1 from the sensor means 12 depends on the number, typology and configuration of said sensor means 12 included in a given configuration of the device 1 or of the system. The number of inputs z must match the number of synapses in the layer $S_0$ of the network R1. Upon each detection, an input z vector will be generated, designated as Z, which will be sent to the layer $S_0$ of the second neural network R1. Depending on the configuration of the sensor means 12, each z will always be sent to the same synapse.

It must be pointed out that the method for collecting the pathology data and the consequent generation of vectors Z is independent of whether the neural networks R1 and R2 are in the training phase or in the operating phase. The same also applies to the image collection method, which remains unchanged whether the first neural network RP is in the training phase or in the operating phase.

The following will describe the operation of the first neural network RP when said network RP is in the training phase. As previously described, the network comprises two layers ($S_{p1}$ and $S_{p2}$) of synapses. The number of synapses $S_{p1\_1}, \ldots, S_{p1\_n}$ and $S_{p2\_1}, \ldots, S_{p2\_n}$ of each layer is given by the number of lesion typologies that the network RP will have to recognize after the training.

Each one of the synapses is connected to three synapse vectors $s_{pr\_1}, s_{pg\_1}, s_{pb\_1}$ and $s_{pr\_2}, s_{pg\_2}, s_{pb\_2}$. With each synapse $s_{pr\_1}, s_{pg\_1}, s_{pb\_1}$ and $s_{pr\_2}, s_{pg\_2}, s_{pb\_2}$ of each vector in both layers $S_{p1}$ and $S_{p2}$ a vector position value is associated, consisting of an index ranging from 1 to 256. If the network is being subjected to the training phase for the first time, then all synapses $s_{pr\_1}, s_{pg\_1}, s_{pb\_1}$ and $S_{pr\_2}, s_{pg\_2}, s_{pb\_2}$ of all nodes will be initialized to a value of 0.

When the photograph is taken, the user must, preferably via the data entry interface, draw a closed line on the image, such that the drawn line is superimposed on those pixels of the taken image which represent the edge of the lesion. For computational reasons, the user may select a region of interest (also referred to as ROI), i.e., an image portion that comprises the lesion and part of the periphery. In that case, the network RP will be trained by considering the ROI as the taken image. Before or after doing this, the user must preferably select, still by using the data entry interface, the typology of the lesion under examination from the list of lesion typologies that the network has to be trained to recognize. Each selectable lesion typology is associated with a pair of synapses. Once the line has been drawn, all the pixels within the contour (called px1) and all the pixels of the image outside the selected contour (called px2) are analyzed by reading the R, G and B values of each one of them. The values of R, G and B of each pixel must fall within a range of 0 to 255.

If the analyzed pixel belongs to the group of pixels px1 and its values of R, G and B are, respectively, r, g and b, the synapses $S_{p\_1}$ in the position r+1, $S_{pg\_1}$ in the position g+1, and $S_{pb\_1}$ in the position b+1, of the synapse $S_{p1\_1}, \ldots, S_{p\_1}$ of the layer $S_{p1}$ corresponding to the lesion selected by the user are incremented by one unit. If the analyzed pixel belongs to the group of pixels px2 and its values of R, G and B are, respectively, r, g and b, the synapses $S_{pr\_2}$ in the position r+1, $S_{pg\_2}$ in the position g+1, and $S_{pb\_1}$ in the position b+1, of the synapse $S_{p2\_1}, \ldots, S_{p2\_n}$ of the layer $S_{p2}$ corresponding to the lesion selected by the user are incremented by one unit. When every image has been analyzed, all the synapses $s_{p\_1}, S_{pg\_1}, S_{pb\_1}$ and $s_{pr\_2}, S_{pg\_2}, S_{pb\_2}$ are normalized according to the following rule:

$$\|S_{p(r,g,b)_d}\| = \frac{S_{p(r,g,b)_d}}{\max_{i=1,\ldots,256}(S_{p(r,g,b)_i})}$$

The neural network RP can be considered as trained if, for each lesion typology that it must be trained to recognize, a number of images equal to or greater than the sum of the synapses $S_{p1\_1}, \ldots, S_{p1\_n}$ and $S_{p2\_1}, \ldots, S_{p2\_n}$ that are present in both layers $S_{p1}$ and $S_{p2}$ have been analyzed.

Once the neural network RP has been trained, the images acquired by the image acquisition means 11 are analyzed pixel by pixel. Before starting the analysis, it is necessary to program a neighbourhood value v, which must be an odd number. The neighbourhood value v may take values ranging from 1 to the total number of pixels of the image under examination. The analyzed pixel is placed within a regular grid composed of $v^2$ pixels. The remaining elements of the grid are occupied by the pixels around the pixel being analyzed. For each one of the pixels in the grid, the respective values of R(=r), G(=g) and B(=b) are analyzed. At his point, the values $S_{p\_1}$ and $S_{pr\_2}$ in the position r+1, $S_{pg\_1}$ and $S_{pg\_2}$ in the position g+1, and $S_{pb\_1}$ and $S_{pb\_2}$ in the position b+1, of the pair of synapses corresponding to a lesion in both the layer $S_{p1}$ and the layer $S_{p2}$ are compared, computing the value F by means of the following formula (1 indicates the pixel sp corresponding to a given lesion typology in the layers $S_{p1}$ and $S_{p2}$):

$$F=(S_{p1}(s_{p-1}(s_{pr-(r+1)}))+S_{p2}(s_{p-1}(s_{pg-g+1)}))+(S_{p1}(s_{p-1}(s_{pg-(g+1)}))+S_{p2}(s_{p-1}(s_{pg-(g+1)}))+(S_{p1}(s_{p-1}(s_{pb-(b+1)}))+S_{p2}(s_{p-1}(s_{pb-(b+1)})),$$

The value F of each pixel is calculated for each pixel in the grid for each synapse $S_{p1\_1}, \ldots, S_{p1\_n}$ and $S_{p2\_1}, \ldots, S_{p2\_n}$ corresponding to each lesion typology. All values F of all pixels in the grid for a given lesion typology are then added together. If for a given lesion typology the value obtained is negative, then the central pixel in the grid will be classified as healthy for that lesion. If the value obtained is positive, then the central pixel in the grid will be classified as positive for that given lesion.

For each lesion typology, the pixels that have turned out to be positive are added together, thereby obtaining the extension of that given lesion typology. The extension value can be translated into the metric system on the basis of the distance of the device 1 from the lesion detected by means of said one or more optical and/or acoustic distance sensors. By comparing the distance value thus obtained with the focal curve of the CMOS camera, it is possible to obtain the area covered by a single pixel of the image. By multiplying that value by the pixels belonging to a given lesion typology, the area of the cutaneous lesion is obtained.

It is apparent from this description that the neural network RP cannot replace the diagnostic activity of a dermatologist, but can support it by highlighting to the physician the various cutaneous diseases that may be depicted in the image acquired by the image acquisition means 11. This will help the dermatologist make a diagnosis of higher quality (in less time).

The following will describe the training phase for the third neural network R2; for this purpose, it must be reminded that said network R1 is formed by the layer $S_0$ and x layers $S_{j-i}$ (where j ranges from 1 to x) and y layers $S_{k-h}$ of synapses (where k ranges from 1 to y). The layers of synapses i are in this phase "trained" to compute, from the data coming from the sensor means 12, the presence of an infective condition of the lesion, while the synapses h are used to compute the presence of an inflammatory condition. The number of synapses in $S_0$ is generally equal to a number $N_0$ which depends, as previously described, on the number and typology of the sensor means 12 installed (or connected) in the specific configuration of the device 1. The synapses of the layers i and k are connected to those of the layer $S_0$ and of the other layers as previously described. All the synapses of the network may take values of 0 to 1, discretized into a number of intermediate values, called steps, which can be modified. The number of steps that the synapses of a given layer can take cannot be smaller than the number of synapses that are present in that very layer. At the beginning of the training of the third neural network R2, the value of all synapses, regardless of the layer they belong to, is set to a value of 0. Between a layer of synapses and the next one, a threshold value $\theta$ is set, which can be adjusted to a value ranging from 0 to 1. In the network taken into account herein, x thresholds $\theta_{j-i}$ (with j ranging from 1 to x) and y thresholds $\theta_{k-h}$ (with k ranging from 1 to y) have been configured. All threshold values $\theta$ may be different from one another, except for $\theta_{1-i}$ and $\theta_{1-h}$, which must have the same value.

It must be pointed out that, for each acquisition made, a vector Z is generated, composed of $N_0$ inputs z, each one inputted to a specific one of the $N_0$ synapses of the layer $S_0$. Also, upon each acquisition a user U (who is preferably a dermatologist) sets, preferably via the data entry means, two desired values, also referred to as desired outputs ($o_i$ and $o_h$). These two values must be respectively set to 1 if there is an infected condition of the lesion or there is an inflamed condition of said lesion. The presence of an infection or an inflammation is established by the operator during the training phase. For each synapse of the layer $S_0$, the weight $w_0$ is computed upon each acquisition as:

$$w_{0-n0}=(z_{n0}s_{0-n0})/N_0,$$

where no is an integer number ranging from 1 to $N_0$. By adding up the weights obtained in the layer $S_0$, one obtains the computational output value $\Sigma_0$, from which a stability value $\Delta_1$ is then calculated by means of either one of the following formulae:

$$\Delta_1=(2\Theta(o_i+o_h)-1)(\Sigma_0-\theta_{1-i})$$

or $$\Delta_1=(2\Theta(o_i+o_h)-1)(\Sigma_0-\theta_{1-h},$$

where $\Theta$ is the Heavyside function. The Heavyside function $\Theta(x)$ returns a null value for negative x and a unitary value for positive x. If $\Delta_1$ is greater than 0, then the weights of the synapses of the layer $S_0$ will remain unchanged. If $\Delta_1$ is smaller than or equal to 0, then the weights of the synapses having an input equal to 1 will go up by one step if $\Theta(o_i+o_h)$ is equal to 1; conversely, if $\Theta(o_i+o_h)$ is equal to zero, the synapses having an input equal to 1 will take a value lower by one step.

If $\Delta_1$ is greater than 0, then the input values z will be transmitted to the two first-line layers $S_{1-i}$, and $S_{1-h}$. The training of these two layers is done by using the same method already adopted for the layer $S_0$. As regards $S_{1-i}$, the weights are computed as follows:

$$w_{1-i-n1_{1\rightarrow N1}}=(z_{n0}s_{1-i-n1})/N_{1-i},$$

whereas for the layer $S_{1-h}$:

$$w_{1-h-n1_{1\rightarrow N1}}=(z_{n0}s_{1-h-n1})/N_{1-h}.$$

where n1 is the identification value of the synapse, which may be an integer number ranging from 1 to $N_1$, considering that $N_1$ is equal to $N_0$, as previously described. The stability values $\Delta_{2-i}$ and $\Delta_{2-h}$ are respectively computed as follows:

$$\Delta_{2-i}=(2o_i-1)(\Sigma_{1-i}-\theta_{2-i}) \text{ oppure } \Delta_{2-h}=(2o_h-1)(\Sigma_{1-h}-\theta_{2-h}).$$

The computational output values of $\Sigma_{1-i}$ and $\Sigma_{1-h}$, equal, respectively, the sum of the values of $\Delta_{2-i}$, and $\Delta_{2-h}$, whereas the values of the synapses of the respective layers are modified by using the same method adopted for the synapses of the layer $S_0$.

The training method is repeated in the same way for the layers following the first-line ones. In general, the weight of each synapse is computed as follows:

$$w_a=(z_a s_a)/N_b,$$

where $z_a$ is the input to the individual synapse, $s_a$ is the value of the individual synapse, and $N_b$ is the number of synapses that are present in the b-th layer. For each layer, the computational value equals the sum of the weights of the synapses of the individual layer, and the stability values are computed by means of the following formula:

$$\Delta_b=(2o_{(i,h)}-1)(\Sigma_b-\theta_{(b+1)}).$$

It must however be pointed out that the inputs to the respective synapses change. Each synapse of the layers following the layers $S_{1-i}$, and $S_{1-h}$ is connected to at least two synapses of the immediately preceding layer. Considering a generic synapse of a layer $S_u$ and the two synapses connected thereto of the preceding layer $S_{1(u-1)}$ and $S_{2(u-1)}$, the input $z_u$ equals $\Theta((w_{1(u-1)}+w_{2(u-1)})-1)$. The two values $w_{1(u-1)}$ and $w_{2(u-1)}$ are, respectively, the weights of the two synapses of the preceding layer. The input values passed on from the preceding layer to the next one will be generated if the stability value turns out to be greater than 0. Otherwise, all the inputs sent to the next layer will have to be considered as null.

The network R1 can be considered as trained when a number of input vectors Z have been sent to the layer $S_0$ which equals at least the total number of synapses comprised in said second network R1.

In the course of the operating phase, the second neural network R1 consists of synapses having the weights obtained during the previous training phase. During this phase, neither such values nor the network structure will change. It is however possible to re-program the threshold values $\theta$ for each layer on condition that the values of $\theta_{1-i}$ and $\theta_{1-h}$ are programmed equal.

In this phase, the input values sent to the individual layers are obtained in the same way as during the training phase. During the acquisition of the pathology data via the sensor means 12 of the device 1, the user does not establish the values of $o_i$ and $o_h$. The pathology data generated by the sensor means 12 are inputted to the layer $S_0$. As in the training phase, the values of the weights of the synapses are computed for each layer as follows:

$$w_a=(z_a s_a)/N_b,$$

whereas the computational output of each layer equals the sum of all weights of that layer. Unlike the previous phase, for each layer an operational output is computed; the operational output of the b-th layer is defined as follows:

$$O_b=\Theta(\Sigma_b-\theta_{(b+1)})(\Sigma_b-\theta_{(b+1)}).$$

If $O_b$ is greater than 0, then the inputs for the next layer will be generated in the same way as in the training phase; otherwise, all the inputs sent to the next layer will be null. Upon a new acquisition, the network R1 will be able to establish that the lesion is infected, if $O_{1-i}$ is greater than 0, and to establish the presence of an inflammation, if $O_{1-h}$ is greater than 0.

The following will describe the training phase for the third neural network R2. As previously described, the purpose of the neural network R2 is to evaluate the degree of the infection and/or inflammation of the lesion by means of a circuit model of human skin. From an electric viewpoint, it is comparable to a memristor, i.e., a non-linear dynamic electric resistor that changes its own state as a function of flux $\varphi(t)=\int_{-\infty}^{n}v(t)dt$ and charge $q(t)=\int_{-\infty}^{n}i(t)dt$. According to this equivalence, the relation that binds the human skin to the memristor can be written as:

$$q(t) = M(\alpha, \varphi(t)) = \frac{c_0 D^2}{\alpha R}\left(1 - \left(1 - \frac{2\alpha\varphi(t)}{\tau c_0^2 D^2}\right)^{1/2}\right).$$

In the above relation, R is the electric resistance of the portion of skin considered (which is proportional to the mean resistivity of the skin and to the size of the portion considered), D is the depth of the skin, and co is a constant. The value $\alpha$ is related to the electric potential and to the presence of ions in the pores and surface of the skin, while $\tau$ depends on the morphological characteristics of the skin. The presence of an inflammatory or infective state can modify these conditions, and therefore it is possible, through the third neural network R2, to link the causes of infection and inflammation (found by means of the network R1) to a. The training phase for the network R2 can only be carried out by using the network R1 in the operating phase.

As previously described, the network R2 consists of a single layer $S_r$ composed of a number of synapses equaling the number of layers that make up the network R1 minus one, in that the operational output value of the layer $S_0$ is not inputted to the network. Considering a network R1 formed by $n_r$ layers, the inputs sent to the nodes consist of the operational output values $O_q$, where q is an integer number ranging from 1 to $n_r-1$. Each synapse of the layer $S_r$ of the network R2 may take real values in the range of $-1$ to 1. The network further comprises an additional synapse which, during the training phase, can be associated with a value that is either computed on the basis of the electromyographic signal or determined empirically. In the former case, upon each acquisition an electric signal compliant with the above-described specifications (to avoid any risk of minishock for the patient) is applied, preferably by means of dry-disk electrodes arranged at a maximum distance of 5 cm on two opposite sides of the lesion under examination. The flux of the applied voltage and the charge of the current detected by the electrodes are then computed. Through the circuit model of skin-memristor equivalence, the value of $\alpha$ is then obtained and assigned to the synapse $s_e$ for that acquisition. If the values of the synapse $s_e$ are established empirically and entered via the interfacing means, the node $s_e$ may take values ranging from 0 to 10 as determined by the user, who will increment the value as the degree of infection and/or inflammation increases.

In the case that during the training phase the values of the node $s_e$ are assigned the value of a obtained through acquisition of the electric signal, then it will be necessary to establish beforehand a basic value $\alpha_0$ thereof. This can be obtained by averaging the values of a obtained through a number of electric signal acquisitions not smaller than the number of nodes $s_r$ that make up the neural network R2 when the lesion is neither inflamed nor infected. If the value of $s_e$ is attributed empirically, then the basic value will be set to 0.

Once the value of $\alpha_0$ has been established through the signal acquisition method, it is possible to proceed with the training of the network by means of the operational output values coming from the layers of the second neural network R1. The synapses of the layer $S_r$ are in turn all connected to an adder synapse $S_{s1}$, to which also the synapse $s_e$ is connected. Upon the first acquisition of the first training phase, all synapses $s_{r-1}, \ldots, s_{r-q}$ are set to a value of 1, and during the same their value will not change. Upon each acquisition, for each synapse the weight is computed as:

$$w_q=(O_q s_{r-q})/N_{r-1},$$

and a computational output $\Sigma_r$ is then computed therefrom, which equals the sum of all weights obtained. From the second acquisition onwards, each $\Sigma_r$ obtained is compared with the $\Sigma_r$ obtained during the previous acquisition. The same comparison is made between the $\alpha$ obtained and the previous one and between all the values of O obtained and the previous ones; in this latter case, the percent increase or decrease thereof is computed. The values of the synapses of the layer $S_r$ are changed in accordance with the following rules:
1. if both $\alpha$ and $\Sigma r$ have increased compared to the previous acquisition, then all those synapses to which a non-null operational output value has been inputted will be increased or decreased in a way directly proportional to the percent increase or decrease obtained in comparison with the same operational output of the previous acquisition;
2. if $\alpha$ has increased compared to the one obtained in the previous acquisition and, on the contrary, $\Sigma r$ has decreased compared to the one obtained in the previous acquisition, or vice versa, then all those synapses to which a non-null operational output value has been inputted will be increased or decreased in a way inversely proportional to the percent increase or decrease obtained in comparison with the same operational output of the previous acquisition.

In the case that the values of the synapse $s_e$ are assigned empirically (i.e., by the dermatologist U), upon every new acquisition it will be necessary to assign to that synapse a value proportional to the observed degree of infection and/or inflammation of the lesion. In this case as well, all the synapses of the layer $S_r$ have a value of 1 at the beginning of the training phase. The method of training and changing the values of the synapses $s_r$ does not change from the previous method.

The training of the network R2 can be considered to be complete when at least a number of acquisitions equaling the number of synapses in the layer $S_r$ have been made.

When the network R2 is in the operating phase, the values of the synapses of the layer $S_r$ are those obtained from the above-described training phase and will not change in operation. In this phase there is no acquisition of the electric signal E by the electromyographic unit or there is no assignment of the empirical value of $\alpha$ to the synapse $s_e$, since it only provides for processing the output data obtained from the network R1 after the acquisitions already carried out. This is possible because, in the course of the operating phase, the memristor model is considered as fully calibrated, thus not requiring any further adjustments.

As in the training phase, upon each acquisition the operational output values of the second neural network R1, except for the one obtained from the layer $S_0$ of the same network, are inputted to each synapse of the layer $S_r$. In this phase as well, the weights of the synapses are obtained as:

$$w_q = (O_q S_{r-q})/N_{r-1},$$

and an operational output $\Sigma_{r2}$ is computed therefrom in the relation synapse $s_{s2}$ to which all synapses of the layer $s_r$ are connected. The value $\Sigma_{r2}$ is then entered into the relation:

$$q(t) = M(\alpha, \varphi(t)) = \frac{c_0 D^2}{\sum_{r2} R}\left(1 - \left(1 - \frac{2\sum_{r2}\varphi(t)}{\tau c_0^2 D^2}\right)^{1/2}\right).$$

The values of q(t) are computed by means of a flow φ(t) obtained from a simulated sinusoidal voltage signal of 40 Volt peak-to-peak at the frequency of 1 Hz, and the curve obtained therefrom is then drawn. Based on said curve one can establish, considering its morphology, the degree of infection or inflammation of the lesion under examination. To this end, the processing means 14 may be configured for establishing the degree of infection or inflammation of the lesion on the basis of the flow φ(t) As an alternative, the flow φ(t) may be displayed on the dermatologist's terminal and/or on visualization means (e.g., an active-matrix display, three-dimensional glasses, or the like) connected to the video interface of the device 1.

The present description has tackled some of the possible variants, but it will be apparent to the man skilled in the art that other embodiments may also be implemented, wherein some elements may be replaced with other technically equivalent elements. The present invention is not therefore limited to the explanatory examples described herein, but may be subject to many modifications, improvements or replacements of equivalent parts and elements without departing from the basic inventive idea, as set out in the following claims.

The invention claimed is:

1. A device for monitoring cutaneous diseases, comprising:
   image acquisition means adapted to acquire medical images of at least one portion of skin affected by a cutaneous disease;
   sensor means adapted to detect physical conditions of said portion of skin and/or environmental conditions around said portion of skin, and to generate pathology data representing said physical conditions and/or said environmental conditions;
   memory means for storing data in digital form; and
   processing means in communication with the image acquisition means, the sensor means and the memory means, wherein said processing means are configured for:
      reading the pathology data detected by the sensor means and the medical images acquired by the image acquisition means, and
      storing said pathology data and said medical images into said memory means;
   wherein the sensor means comprises:
   one or more distance sensors configured to measure a distance between said portion of skin and said device and measure a three-dimensional profile of said portion of skin, and/or
   an electronic nose adapted to detect the presence of volatile compounds emitted by said at least one portion of skin affected by said cutaneous disease, and/or
   an electromyographic unit capable of acquiring an electromyographic signal, wherein the processing means are configured for executing a first portion of code implementing a first neural network trained to produce, on the basis of said pathology status data and said electromyographic signal, a pathologic degree datum defining the degree of the infection and/or inflammation of said portion of skin affected by said cutaneous disease.

2. The device according to claim 1, wherein the sensor means comprise an ultraviolet image sensor capable of detecting light having a wavelength in the range of 200 to 450 nanometers, and one or more sources of ultraviolet light.

3. The device according to claim 1, wherein the sensor means comprise an infrared image sensor capable of detecting light having a wavelength in the range of 650 to 1,200 nanometers, and one or more sources of infrared light.

4. The device according to claim 1, wherein the sensor means comprise one or more thermal sensing device capable of sensing the surface temperature of said at least one portion of skin affected by said cutaneous disease.

5. The device according to claim 1, wherein the sensor means comprise at least one humidity sensor capable of sensing the humidity of said portion of skin affected by said cutaneous disease.

6. The device according to claim 1, wherein the memory means contain at least acquisition data specifying how the images must be acquired by said image acquisition means and/or how the physical and/or environmental conditions must be detected by said sensor means, and wherein the image acquisition means are configured for acquiring medical images on the basis of said acquisition data and/or the sensor means are configured for detecting the physical conditions of said portion of skin and/or the environmental conditions around said portion of skin on the basis of said acquisition data.

7. The device according to claim 1, comprising communication means for communicating with a processing apparatus.

8. The device according to claim 7, wherein the processing means are configured for:
   receiving, through the communication means, the acquisition data, and
   storing said acquisition data into the memory means.

9. The device according to claim 1, wherein the processing means are configured for executing a second portion of code implementing a second neural network trained to produce, on the basis of said medical images, a typology datum defining a typology of said cutaneous disease.

10. The device according to claim 1, wherein the processing means are configured for executing a third portion of code implementing a third neural network trained to produce, on the basis of said pathology data, pathology status data defining if said portion of skin affected by said cutaneous disease is infected and/or inflamed.

11. A system comprising a device for monitoring cutaneous diseases, wherein said device comprises:
   image acquisition means adapted to acquire medical images of at least one portion of skin affected by a cutaneous disease;
   sensor means adapted to detect physical conditions of said portion of skin and/or environmental conditions around said portion of skin, and to generate pathology data representing said physical conditions and/or said environmental conditions;

memory means for storing data in digital form; and processing means in communication with the image acquisition means, the sensor means and the memory means, wherein said processing means are configured for:

reading the pathology data detected by the sensor means and the medical images acquired by the image acquisition means, and storing said pathology data and said medical images into said memory means;

communication means for communicating with a processing apparatus; and said processing apparatus, wherein said device is configured for transmitting the pathology data, through the communication means, to said processing apparatus, and wherein said processing apparatus is configured for executing a first portion of code implementing a first neural network trained to produce, on the basis of said pathology data, pathology status data defining if said portion of skin affected by said cutaneous disease is infected and/or inflamed, and wherein the sensor means of the device comprise an electromyographic unit capable of acquiring an electromyographic signal, and wherein said processing apparatus is configured for executing a second portion of code implementing a second neural network trained to produce, on the basis of said pathology status data and said electromyographic signal, a pathologic degree datum defining the degree of the infection and/or inflammation of said portion of skin affected by said cutaneous disease.

12. A system comprising the device according to claim 11, and said processing apparatus, wherein said device is configured for transmitting the medical images, through the communication means, to said processing apparatus, and wherein said processing apparatus is configured for executing a third portion of code implementing a third neural network trained to produce, on the basis of said medical images, a typology datum defining the typology of said cutaneous disease.

13. A method for monitoring cutaneous diseases, comprising:

an image acquisition phase, wherein medical images of at least one portion of skin affected by a cutaneous disease are acquired by image acquisition means;

a physical-environmental data acquisition phase, wherein physical conditions of said portion of skin and/or environmental conditions around said portion of skin are detected by sensor means, and pathology data are generated which represent said physical conditions and/or said environmental conditions; and a storage phase, wherein the pathology data detected by the sensor means and the medical images acquired by the image acquisition means are read by processing means, and said pathology data and said medical images are stored into memory means, and an operating phase, in which neural networks can autonomously process data collected by the image acquisition means and by the sensor means, wherein the sensor means comprises:

one or more distance sensors configured to measure a distance between said portion of skin and said device and measure a three-dimensional profile of said portion of skin, and/or an electronic nose adapted to detect the presence of volatile compounds emitted by said at least one portion of skin affected by said cutaneous disease, and/or an electromyographic unit capable of acquiring an electromyographic signal, wherein during the operating phase, a first neural network, which has been trained to produce, on the basis of said pathology status data and said electromyographic signal, a pathologic degree datum defining the degree of the infection and/or inflammation of said portion of skin affected by said cutaneous disease, processes said data collected by the image acquisition means and by the sensor means.

14. The method according to claim 13, wherein, during the image acquisition phase and/or the physical-environmental data acquisition phase, the medical images and/or the physical conditions of said portion of skin and/or the environmental conditions around said portion of skin are acquired on the basis of acquisition data specifying how the images must be acquired by said image acquisition means and/or how the physical and/or environmental conditions must be detected by said sensor means.

15. A computer program product which is loaded into non-transitory memory of an electronic computer, and which comprises portions of software code for executing the phases of the method according to claim 13.

* * * * *